(12) United States Patent
Weckström et al.

(10) Patent No.: US 7,132,658 B2
(45) Date of Patent: Nov. 7, 2006

(54) DETECTION ASSEMBLY AND MEASURING ARRANGEMENT FOR MULTIGAS ANALYZERS

(75) Inventors: Kurt Weckström, Esbo (FI); Kai Karlsson, Helsinki (FI)

(73) Assignee: Instrumentarium Corp., Helsinki (FI)

( * ) Notice: Subject to any disclaimer, the term of this patent is extended or adjusted under 35 U.S.C. 154(b) by 276 days.

(21) Appl. No.: 10/857,631

(22) Filed: May 28, 2004

(65) Prior Publication Data

US 2005/0012042 A1    Jan. 20, 2005

(30) Foreign Application Priority Data

May 30, 2003    (EP) ................... 03396052

(51) Int. Cl.
*G01J 5/02*    (2006.01)
*A61B 5/08*    (2006.01)

(52) U.S. Cl. .......... 250/339.13; 600/529; 600/532

(58) Field of Classification Search ........... 250/333, 250/334, 338; 600/529
See application file for complete search history.

(56) References Cited

U.S. PATENT DOCUMENTS

| | | | |
|---|---|---|---|
| 4,914,719 A | 4/1990 | Conlon et al. | |
| 5,146,092 A | 9/1992 | Apperson et al. | |
| 5,464,982 A * | 11/1995 | Drucker et al. | 250/343 |
| 5,811,812 A | 9/1998 | Williams et al. | |
| 6,469,303 B1 * | 10/2002 | Sun et al. | 250/343 |
| 6,955,652 B1 * | 10/2005 | Baum et al. | 600/532 |
| 2002/0036266 A1 | 3/2002 | Dreyer et al. | |
| 2003/0205673 A1 * | 11/2003 | Williams | 250/343 |

FOREIGN PATENT DOCUMENTS

| EP | 0 635 745 | 1/1995 |
|---|---|---|
| EP | 1 288 700 | 3/2003 |

OTHER PUBLICATIONS

Naumann/Schröder: Bauelemente der Optik, Bild 5.8.1 c, Carl Hanser verlag, 1987, pp. 185-187.
Walter Driscoll, William Vaughan: Handbook of Optics, Chapters 104-106, McGraw-Hill Book Company, 1987.

* cited by examiner

*Primary Examiner*—David Porta
*Assistant Examiner*—David S. Baker
(74) *Attorney, Agent, or Firm*—Andrus, Sceales, Starke & Sawall, LLP

(57) ABSTRACT

A non-dispersive infrared measuring arrangement for a multigas analyzer is described having a radiation source (10), a measuring chamber (20), a beam splitter (3), at least a first and a second detector unit (21, 22) both with at least two detectors (1a, 1b; 2a, 2b); and optical filters in radiation beam portions ending in said detectors. The detector units receive the reflected beam portions ($R_R$) and the transmitted beam portion ($R_T$). Both the first and second detector units (21, 22) have: at least one measuring detectors (1a, 1b) provided with an optical measurement filter (5a, 5b); and at least one reference detectors (2a, 2b) provided with an optical reference filter (6a, 6b). Alternatively, the first detector unit (21) has at least two measuring detectors (1a, 1b) each provided with an optical measurement filter (5a, 5b), and the second detector unit (22) has at least two reference detectors (2a, 2b) each provided with an optical reference filter (6a, 6b). The first detector in said first detector unit and said second detector in said second detector unit are positioned to constitute a first independent single path analyzer channel (11), and said second detector in said first detector unit and said first detector in said second detector unit are positioned to constitute a second independent single path analyzer channel (12).

72 Claims, 3 Drawing Sheets

DETECTION ASSEMBLY AND MEASURING ARRANGEMENT FOR MULTIGAS ANALYZERS

CROSS REFERENCE TO RELATED APPLICATION

The present application claims priority from European Patent Application No. 03396052.7, filed May 30, 2003.

FIELD OF THE INVENTION

The present invention relates to infrared multigas analyzers that measure concentrations of the desired gas components in the gas sample and may also identify the presence of some gas components. More specifically, the present invention relates to a detection assembly for a non-dispersive infrared multigas analyzer, comprising: a beam splitter for dividing an IR-radiation beam into at least one reflected beam portion and at least one transmitted beam portion, at least a first and a second detector unit both with at least two separate detectors respectively, and optical filters in front of said detectors; said detector units being positioned to receive said at least one reflected beam portion and said at least one transmitted beam portion respectively. The present invention also relates to a non-dispersive infrared measuring arrangement in a multigas analyzer, comprising: a radiation source providing an IR-radiation beam; a measuring chamber for receiving a gas mixture to be analyzed, and adapted to transmission of said radiation beam; a beam splitter dividing said beam into at least one reflected beam portion and at least one transmitted beam portion; at least a first and a second detector unit both with at least two detectors; and optical filters positioned in said beam or beam portions ending in said detectors, said detector units being directed to receive said at least one reflected beam portion and said at least one transmitted beam portion respectively.

This invention is preferably applied in clinical non-dispersive infrared multigas analyzers of the mainstream type but it can also be applied in other types and applications of gas analyzers.

BACKGROUND OF THE INVENTION

In a non-dispersive infrared (=NDIR) gas analyzer the measurement is based on the absorption of infrared (=IR) radiation in the gas sample. A radiation source directs a beam of infrared radiation through a measuring chamber to a radiation detector whose output signal depends on the strength of the absorption of radiation in the sample gas. The optical wavelength band used for the measurement is selected non-dispersively with an optical bandpass filter. The radiation source typically consists of an electrically heated filament and radiation collecting optics. The gas mixture to be analyzed, i.e. the sample gas, is fed through the measuring chamber, whereupon the gas mixture is contained in the chamber for analysis. The measuring chamber can be a tubular space provided with entrance and exit windows that are transparent at the measurement wavelength and with inlet and outlet for the sample gas. Radiation is absorbed by the gas sample when passing through the measuring chamber.

The radiation detector generates an electric signal that depends on the radiation power falling on its sensitive area. The detector type in a gas analyzer depends on its measurement wavelength, as well as on its construction and operating principle. To make the detector's output signal sensitive to a certain gas component, the wavelength band of radiation coming to the detector is selected so that the gas component absorbs radiation on it. This selection is made using an Optical Bandpass Filter (OBF) whose Bandwidth (BW) is typically 1%–2% of the Center Wavelength (CWL).

In NDIR multigas analyzers, the absorption of the gas sample is measured at several wavelength bands, selected to match the absorption spectra of the gas components of interest. This can be accomplished by using one radiation detector and changing the OBFs on the optical path. It is also possible to use several radiation detectors, combined with their corresponding OBFs. In addition to these measurement detectors, there may be one or more reference detectors. The reference detectors typically receive radiation from the radiation source at wavelength bands where the sample gas is known to have no absorption.

To measure the strength of absorption, it is necessary to know the zero levels of the analyzer at the measurement wavelengths. The zero level is the detector signal obtained at a wavelength when the sample gas does not absorb IR-radiation at that wavelength. The strength of absorption is calculated by forming the ratio between the zero level and the detector signal. Mechanical stresses or shocks, as well as changes in the analyzer's temperature can change the output characteristics of the radiation source and change the zero levels. The sensitivity of IR radiation detectors may depend on their operating temperature, which causes changes to the zero levels. Contamination of the measuring chamber may also change the zero levels. Thus, the zero levels or their estimates must be either continuously measured or updated at regular intervals, typically in the order of some tens of minutes.

It is possible to update the zero levels by zeroing the analyzer. This can be performed by measuring the detector signals when the measuring chamber is filled with a so-called zero gas that is known to not absorb radiation at the measurement wavelengths. The measured zero levels are then used as estimates for the real zero levels until the next zeroing. Zeroings interrupt the analyzer's normal operation typically for several seconds. It is not possible to zero a clinical gas analyzer of the mainstream type because the measuring chamber is all the time located in the patient's breathing circuits, whereupon it is not possible to fill the measuring chamber with zero gas.

It is also possible to obtain estimates for the zero levels without zeroing the analyzer. This can be accomplished by the use of reference filters, whereupon the detector signals are measured at reference wavelengths where the gas sample is known to never absorb IR radiation. It is also possible to use separate reference detectors together with reference filters and use the output signals of the reference detectors as estimates for the zero levels at the measurement wavelengths. These estimates are continuously available, together with the detector signals obtained at the measurement wavelengths. It is often sufficient to use one common reference wavelength for all measurement wavelengths. However, if the measurement wavelengths are widely separated form each other, it may be necessary to use more than one reference wavelength.

A clinically used gas analyzer of the mainstream type is operating on the breathing circuit of the patient, whereupon the whole volume or at least the main portion of the breathing air or gas mixture flows through the analyzer and its measuring chamber. Because the measuring chamber is on the breathing circuit, it is easily contaminated by mucus or condensed water. Thus, it is necessary to use one or more reference wavelengths in a mainstream analyzer in order to have good enough estimate for the zero level continuously available.

A clinical mainstream gas analyzer must be small, light, accurate and reliable. It is not possible to zero it during its normal operation. Yet, the analyzer must maintain its accuracy even if the measuring chamber would be contaminated. Due to these requirements, only single gas analyzers for carbon dioxide $CO_2$ have been available and no multigas analyzers of the mainstream type have been commercially available.

Non-dispersive infrared (NDIR) gas analyzers can be divided to two main types according their optical configuration: dual path analyzers and single path analyzers.

FIG. 8A shows the known principle of the dual path analyzer with one operating wavelength. The analyzer has a radiation source 100, a measuring chamber 101, a reference cell 102, an optical bandpass filter 103, a first radiation detector 105 receiving radiation through the measuring chamber, and a second radiation detector 106 receiving radiation through the reference cell. The reference cell is at all times filled with a gas that has no absorption at the operating wavelength of the analyzer. The essential operating principle of dual path analyzers is that an estimate for the zero level is obtained by blocking the optical path through the measuring chamber and measuring the output signal of the detector when radiation comes to it from the source through the reference cell. In the example of FIG. 8A, this is accomplished by moving the optical bandpass filter 103 to come between the reference cell 102 and the second radiation detector 106. In normal operation, filter 103 is located between the measuring chamber 101 and the first detector 105. The optical and mechanical construction of a dual path analyzer is quite complicated. Problems caused by the contamination of the measuring chamber cannot be solved by the dual path construction. Thus, the dual path construction is generally not used in mainstream gas analyzers.

FIG. 8B shows the known principle of the virtually single path analyzer that can be used as mainstream gas analyzer. The measurement filter 103 has a passband where the gas component of interest absorbs radiation and it is constantly located in front of the measurement detector 105. Filter 103 and detector 105 forms the measurement channel of the analyzer. The reference filter 104 with a passband within which the gas sample does not absorb radiation is located in front of the reference detector 106. Filter 104 and detector 106 forms the reference channel of the analyzer. Radiation form the source 100 passes the measuring chamber 101 and optical filters 103 and 104 and falls on the detectors 105 and 106 respectively. The strength of the absorption can be continuously defined by calculating the ratio between the output signals of the reference and measurement detectors. The benefit of this construction is that it has no moving mechanical parts. Also, signals at both the measurement and reference wavelengths are continuously available. However, the optical paths between the source 100 and the two detectors 105 and 106 are not identical through the measuring chamber. This makes the analyzer sensitive to the contamination of the measuring chamber. The drawback of non-identical optical paths through the measuring chamber can be overcome by using a beam splitter to form a true single beam analyzer, which known alternative is shown in FIG. 8C. Radiation from the source 100 passes the measuring chamber 101 and falls on the beam splitter 107.

Beam splitter 107 transmits part of the radiation to the reference channel formed by second filter 104 and the second detector 106, and reflects part of the incoming radiation to the measurement channel formed by the first filter 103 and the first detector 105. Accordingly, the measurement and reference channels have identical optical paths through the measuring chamber. The drawback of the beam splitter construction is that the beam splitter decreases the radiation input to the detectors and the analyzer's signal to noise ratio gets worse approximately by a factor of two.

U.S. Pat. No. 4,914,719 discloses a single path, multi gas analyzer utilizing a plurality of beam splitters. The analyzer described comprises, for N gases having overlapping absorption spectra where N is an integer greater than 1, a sample cell adapted to contain a gas to be analyzed and a source operative to generate at least one measuring beam which passes through the sample cell, the improvement comprising: means, responsive to the at least one measuring beam, for generating N measuring signals, each indicative of optical energy from the source transmitted through the sample cell in a respective optical region characterized by a respective optical center wavelength $\lambda_i$ and a respective bandpass $\Delta\lambda_i$, where i is an integer greater than 0 and less than or equal to N; means, responsive to the N measuring signals, for combining the N measuring signals to automatically determine which of the N gases is present in the sample cell in the greatest concentration and the concentration thereof. Each of the N measuring signals is indicative of no absorbance in the respective optical region. Said $\lambda_i$ and $\Delta\lambda_i$, are selected such that each of the N measuring signals is a substantially linear function of concentration of each of the N gases in the sample cell. Each of the N gases is characterized by significant absorption in each of the N optical regions. The second means comprises means for algebraically combining the N measuring signals to determine the concentration of each of the N gases in the sample cell. However, this publication does neither discuss at all about the necessity of the reference signal, nor disclose any suggestions for the purpose. The disclosed analyzer uses several beam splitters in series, which causes further decrease of the radiation input to the detectors still worsening the signal to noise ratio of the analyzer.

US patent application 2002/0036266 discloses infrared optical multigas analyzers mainly of the dual path or multi path principle, but also one alternative according to, in a way, the single path principle. The analyzers comprise, in general: an infrared optical radiation source arrangement; a first multispectral detector; a second multispectral detector; a cuvette containing the gas mixture to be measured, said infrared optical radiation source being positioned such that the radiation emitted in a first wavelength range reaches the first multispectral detector through the interior space of the cuvette and radiation emitted in a second wavelength range reaches the second multispectral detector through the interior space of the cuvette, said first wavelength range and said second wavelength range being selected such that they will be different from one another. In the main alternatives of this infrared optical gas analyzer the arrangement comprises a first infrared optical radiation source positioned such that the radiation emitted in the first wavelength range reaches the first multispectral detector through the interior space of the cuvette and second radiation source provided such that the radiation emitted in the second wavelength range reaches the second multispectral detector through the interior space of the cuvette. According to the deviating alternative the infrared radiation emitted by the infrared optical radiation source is passed through an entry window into the cuvette, through the interior space of the cuvette, and then the first part of the radiation goes through the dichroic beam splitter reaching the first multispectral detector from there. The second part of the infrared radiation that is not passed through the dichroic beam splitter is reflected at the dichroic beam splitter and passes from there through the interior space of the cuvette through the exit window, which is transparent to infrared light, to reach the second multispectral detector. This publication, either, does not discuss at all about the necessity of the reference signal, nor disclose any suggestions for the purpose, but is directed to detecting the absorption spectra of the several gas components only. In the disclosed analyzer there is either multiple parallel paths through the cuvette, or multiple serial paths through the cuvette. The latter alternative brings one window surface, which is not common to the path and accordingly a potential source of error caused by contamination, and the surface of dichroic beam splitter towards the interior of the cuvette, which beam splitter surface both reflects and transmits and accordingly is a potential source of error caused by contamination, because contamination of this surface has different effect on the reflected radiation part than on the transmitted radiation part. The path lengths through the cuvette into the first multispectral detector and to the second multispectral detector are different. Accordingly, this deviating alternative is not a genuine single path analyzer.

SUMMARY OF THE INVENTION

The object of this invention is to provide a compact and lightweight detection assembly and measuring arrangement for a multigas NDIR analyzer and to minimize its sensitivity to the contamination of the measuring chamber. Another object of the invention is to provide a compact and lightweight detection assembly and measuring arrangement without moving mechanical parts. A third object of the invention is to provide a detection assembly to a multigas NDIR analyzer so that its optical construction does not limit the selection of the IR radiation detector type. A fourth object of the invention is to provide a detection assembly and measuring arrangement for a multigas analyzer, in which the measurement and reference wavelengths can be selected to optimally match the requirements set by the application of the analyzer. A further object of the invention is to set as few as possible limits to the selection of the types and constructions of the other main components of the NDIR gas analyzer.

According to the first aspect of the invention the detection assembly is such that: Said first detector unit and said second detector unit both have at least one first detector, said first detectors being measuring detectors each provided with an optical measurement filter, which has a transmission wavelength band in the range of the absorption band of a gas component, so as to affect that portion of the IR-radiation ending into said first detector; said first detector unit and said second detector unit both have at least one second detector, said second detectors being reference detectors each provided with an optical reference filter, which has a transmission wavelength range, within which said gas component does not have a substantial absorption, so as to affect that portion of the IR-radiation ending into said second detector; and said first detector in said first detector unit and said second detector in said second detector unit are positioned to constitute a first independent single path analyzer channel, and said second detector in said first detector unit and said first detector in said second detector unit are positioned to constitute a second independent single path analyzer channel.

According to the second aspect of the invention the detection assembly is such that: Said first detector unit has at least two first detectors, said first detectors being measuring detectors each provided with an optical measurement filter, which has a transmission wavelength band in the range of the absorption band of a gas component, so as to affect that portion of the IR-radiation ending into said first detector; said second detector unit has at least two second detectors, said second detectors being reference detectors each provided with an optical reference filter, which has a transmission wavelength range, within which said gas component does not have a substantial absorption, so as to affect that portion of the IR-radiation ending into said second detector; and said first detector in said first detector unit and said second detector in said second detector unit are positioned to constitute a first independent single path analyzer channel, and said second detector in said first detector unit and said first detector in said second detector unit are positioned to constitute a second independent single path.

According to the third aspect of the invention the measuring arrangement is such that: Said first detector unit and said second detector unit both have at least one first detector, said first detectors being measuring detectors each provided with an optical measurement filter as said filters having transmission wavelength bands adapted to detection of the concentration of a gas component in said gas mixture; said first detector unit and said second detector unit both have at least one second detector, said second detectors being reference detectors each provided with an optical reference filter as said filters having transmission wavelength ranges, within which said gas component does not have substantial absorption; and aid first detector in said first detector unit and said second detector in said second detector unit are positioned to constitute a first independent single path analyzer channel, and said second detector in said first detector unit and said first detector in said second detector unit are positioned to constitute a second independent single path analyzer channel.

According to the fourth aspect of the invention the measuring arrangement is such that: Said first detector unit has at least two first detectors, said first detectors being measuring detectors each provided with an optical measurement filter as said filters having transmission wavelength bands adapted to detection of the concentration of a gas component in said gas mixture; said second detector unit has at least two second detectors, said second detectors being reference detectors each provided with an optical reference filter as said filters having transmission wavelength ranges, within which said gas component does not have substantial absorption; and said first detector in said first detector unit and said second detector in said second detector unit are positioned to constitute a first independent single path analyzer channel, and said second detector in said first detector unit and said first detector in said second detector unit are positioned to constitute a second independent single path analyzer channel.

The beam splitter's operation is preferably based on transmission and reflection of the incoming radiation. The beam splitter is made of such material and having such a treatment on its surfaces that one part of the incoming radiation is passing through the beam splitter to the first detector unit and another part is reflected from its surfaces to the second detector unit. The splitting ratio of a beam splitter can be defined as the ratio between the transmitted and reflected radiation intensities. The splitting ratio used of the beam splitter of this invention can depend on the wavelength but it can also be substantially independent of the wavelength. The beam splitter can also have one or more areas with wavelength dependent splitting ratio and one or more areas with wavelength independent splitting ratio.

The first detector unit contains at least two individual detectors or detector elements with their respective optical filters, typically bandpass filters, for making each detector or detector element sensitive at one of the wavelength bands used in the NDIR gas analyzer. The second detector unit contains at least two detectors or detector elements with their respective optical filters, typically bandpass filters, for making each detector or detector element sensitive at one of the wavelength bands used in the NDIR multigas analyzer. The first and second detector units are preferably built by integrating the detector elements or detectors and their respective optical filters into two common detector cans.

A measurement channel in a NDIR multigas sensor in essentially formed by the measurement filter passing radiation to the measuring detector. The passband of a measurement filter is selected so that at least one gas component of interest absorbs radiation at it. A reference channel in a NDIR multigas sensor consists of the reference filter passing radiation to the reference detector. The pass bands or limiting bands, or the high pass or low pass characteristics of the reference filters are selected so that the gas sample never absorbs radiation at them.

The detection assembly according to the present invention is built by combining the beam splitter and the first and second detector units so that a measurement partial channel in one detector unit always has a corresponding reference partial channel in the other detector unit. The measurement partial channel and the corresponding reference partial channel are located in their respective detector units so that the radiation falling to the measurement detector and the corresponding reference detector has a common optical path through the sample cell or measuring chamber. In this way, the measurement and reference partial channels are equally affected by the contamination on the measuring chamber and thus, the ratio between the signals from the reference and measurement channels remains unchanged. The type of the broadband radiation source and its modulation or chopping arrangements is not limited by this invention. Also, the type of the IR radiation detectors can be selected without limitations set by the present invention.

BRIEF DESCRIPTION OF THE DRAWINGS

The foregoing summary, and the following detailed description of the preferred embodiments of the present invention, will be better understood when read in conjunction with the accompanying drawings, in which.

DETAILED DESCRIPTION OF THE PREFERRED EMBODIMENTS

Figure 1:
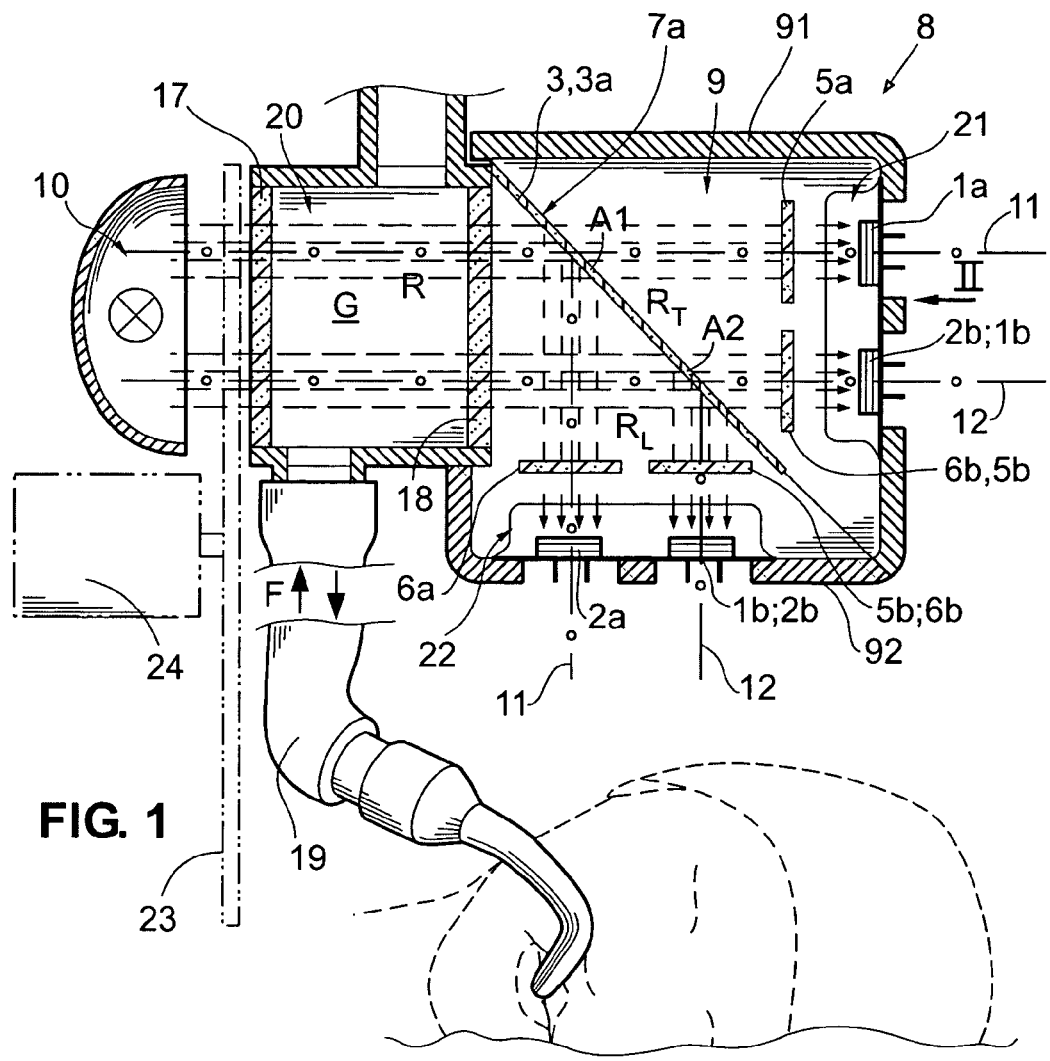
FIG. 1 represents schematically the first embodiment of the measuring arrangement including the detection assembly according to the invention, in mainly longitudinal section I of FIG. 6A parallel to the radiation beams.

In the following FIGS. 1 to 3 and 5 to 6B, the detection assembly 9 and measuring arrangement 8 according to the invention is represented for two measurement and reference channels, i.e. two independent single path analyzer channels 11, 12 for simplicity and legibility of the drawings. The first independent single path analyzer channel 11 have a true single beam or beam section through the measuring chamber, as do the second single path analyzer channel 12. In the FIG. 6C there is shown four independent single path analyzer channels 11 to 14 of the detection assembly 9, but not all parts of the measuring arrangement 8. It shall be understood that those parts of the measuring arrangement not shown are similar or analogous to the respective parts of the two channel embodiments shown in FIGS. 1 to 3 and 5 to 6B. The present invention employs detector units 21, 22, 23, 24 etc. within the detection assembly 9, each detector unit having at least a first detector $1a$, $1b$, $1c$ . . . and a second detector $2a$, $2b$, $2c$ . . . , or at least two first detectors $1a$, $1b$, $1c$ . . . and at least two second detectors $2a$, $2b$, $2c$ . . . . The detectors in a detector unit are separate from each other so as to enable outputting of different signals from depending on the radiation intensity falling on them. Each independent single path analyzer channel 11, 12, 13 etc. has at least a first detector and a second detector arranged and connected as detector pairs $1a+2a$, $1b+2b$, $1c+2c$, $1d+2d$ etc., though it is also possible to use more than two detectors for each analyzer channel. It shall be also understood that the number M of single path analyzer channels, can be any number greater than two. The number M of analyzer channels is at least equal to the number N of those gas components to be analyzed from the gas mixture G flowing through the measuring chamber 20 of the measuring arrangement.

Figure 4A:
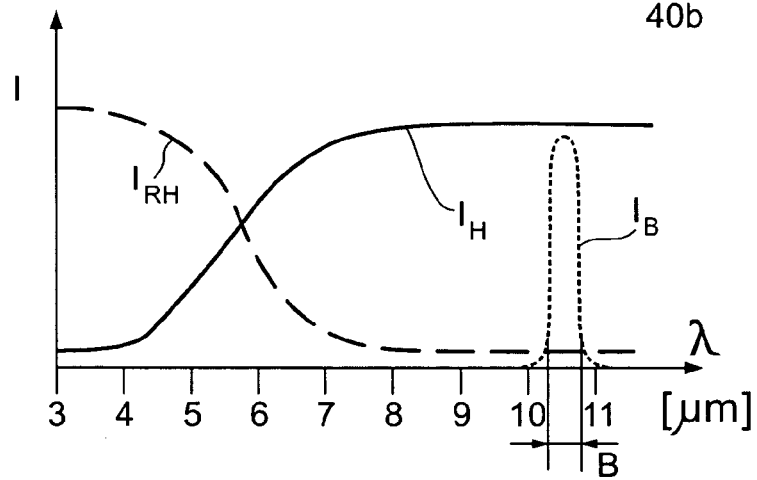
FIGS. 4A and 4B visualize graphically the transmission and reflection properties of the various types of the beam splitter, and the transmission properties of some types of the optical filters utilized in the measuring arrangement and the detection assembly according to the invention.
Figure 4B:
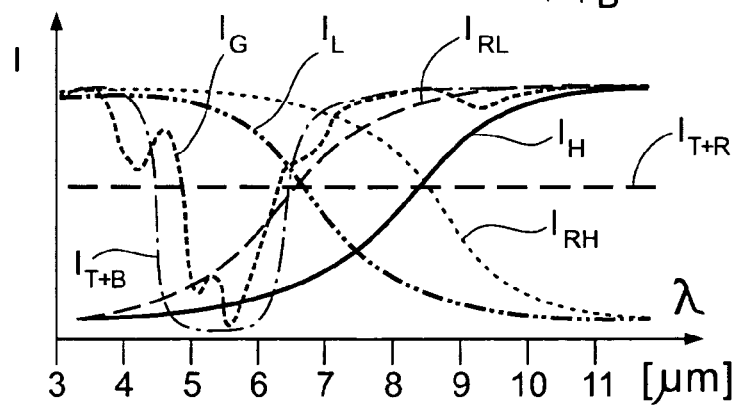

The present invention further employs a beam splitter 3 within the detection assembly 9. The reference number 3 means the beam splitter generally, and the modified reference numbers $3a$, $3b$ and 3.1, 3.2 or the like mean various structures, operating principles or configuration of the beam splitter 3. The beam splitters 3 utilized for dividing the IR-radiation beam R, which has passed through the measuring chamber 20, into at least one reflected beam portion $R_R$ and one transmitted beam portion $R_T$ are preferably physical beam splitters, which are semitransparent mirrors of a proper type, e.g. dichroic mirrors functioning on the same principal as interference filters, or partly transparent coatings not causing interference, or boundary surface(s) of prism(s) or plate(s), which kind of beam splitters are generally known and commercially available. Accordingly, the structures and principles of physical beam splitters are not described in detail. Beam splitters 3, 3a based on semitransparent coatings 7a, e.g. extremely thin metallic coating, not causing interference, and on boundary surface(s) of prism(s) or plate(s) has a substantially even transmittance and reflectance distribution $I_{T+R}$ over a wide wavelength range, as shown in FIG. 4B, they do not divide the falling radiation spectrum to wavelength bands. Then the transmitted portion $R_T$ of the radiation R has the same even or homogenous intensity distribution over the wavelength range in question as the reflected portion $R_R$ of the radiation R. Beam splitters 3, 3b based on dichroic coating 7b, and the interference filters 5a, 5b, 6a, 6b respectively, transmit radiation either over a wavelength band B limited both to longer and shorter wavelengths meaning bandpass $I_B$ characteristics, or over a wavelength range limited to shorter wavelengths meaning highpass $I_H$ characteristics, or over a wavelength range limited to longer wavelengths meaning lowpass $I_L$ characteristics, or limited both from longer and shorter wavelengths meaning bandlimiting $I_{T-B}$ characteristics, as shown in FIGS. 4A and 4B. When the "interference filter" is utilized as the optical filter, either measurement filter 5a, 5b or reference filter 6a, 6b, separate from the beam splitter 3=3a or 3b, its surface is positioned perpendicular to the main beam direction of the radiation R or $R_R$ or $R_T$, whereas when utilized as the beam splitter 3, its surface is positioned in tilted position to have an angle, i.e. angle between the surface and the main beam direction of the radiation, which angle is typically between 30° and 60°, preferably 45°. In this tilted beam splitter position the "interference filter" reflects those wavelengths not transmitted therethrough, and accordingly the "filter" provides inverse characteristics to the reflected beam portion $R_R$. Then the transmitted portion $R_T$ of the radiation R has a first specific intensity distribution over the wavelength range, which first specific intensity distribution deviates from the second specific intensity distribution present in the reflected portion $R_R$ of the radiation R. In the non-tilted optical filter position the reflected wavelength distribution of the "interference filter" is unessential, because not utilized for detection. Of course the "interference filter" absorbs a portion of the falling radiation R or $R_R$ or $R_T$. As already mentioned the detection assembly 9 is provided with optical filters 5a, 5b, 6a, 6b etc., and the optical filters are arranged in front of the detectors, as seen in the radiation direction R, typically between the beam splitter and the detector or detectors, or as the beam splitter. Of course optical filters other than those intended for the analysis of the gas components in the gas mixture or for the reference purposes of the same can be arranged in front of the beam splitter 3, too. The optical filters used as the measurement filters 5a, 5b etc. are bandpass filters with passband characteristics $I_B$ matched with the absorption peak of that gas components, which is measured with that optical filter, as generally known. The optical filters used as the reference filters 6a, 6b etc. can be bandpass filters with passband characteristics $I_B$, or highpass filters with highpass characteristics $I_H$, or lowpass filters with lowpass characteristics $I_L$, or bandlimiting filters with some kind of bandlimiting characteristics $I_{T-B}$, or $I_G$, which characteristics are arranged to deviate from the absorption peak of that gas components, which is measured in the single path analyzer channel in question, as generally known. The optical measurement filters 5a, 5b and reference filters 6a, 6b discussed, if separate from the beam splitter, are positioned between the beam splitter 3 and the detectors. Of course, it is possible to use additional filters, not being measurement filters and reference filters according to the invention, between the radiation source and the beam splitter.

Physical beam splitters 3 have the advantage that the reflected beam portions $R_R$ and the respective transmitted beam portions $R_T$ originate exactly from the same volume or area of the measuring chamber 20. When the detector units 21 and 22, or 21-24, are properly aligned to receive the reflected radiation and the transmitted radiation from the same or common beam splitter areas A1 and A2, or A1-A4 respectively, the full advantage is attained from using the physical beam splitter(s). Geometrical beam splitters can be also used. In this case the reflected beam portions $R_R$ and the respective transmitted beam portions $R_T$ does not originate exactly from the same volume or area of the measuring chamber, but by a proper configuration of the beam splitter the deviations between the reflected beam portions and the transmitted beam portions in respect to the volume or area of the measuring chamber would be so small that they can be neglected in practice for many applications. For this purpose the geometrical beam splitter shall have a plurality of holes 76, i.e. areas C transparent to radiation, at least within each of the common beam splitter areas A1 and A2, or A1–A4, the rest of the beam splitter being a reflective area D. This kind of beam splitters are known, e.g. Naumann/Schröder: Bauelemente der Optik, Bild 5.8.1 c)—Carl Hanser Verlag, 1987 and EP-0 635 745, and are commercially available. The geometrical beam splitters are, accordingly, not described in detail. These types of geometrical beam splitters mentioned can be used in the embodiments of FIGS. 1 and 5 instead of the physical beam splitters functioning on the basis of semi-transparent coating or boundary surface without the interference effect of the radiation waves as mentioned above. It might be possible that geometrical beam splitters having configuration of a grating, grid or mesh, as described in Walter Driscoll, William Vaughan: Handbook of Optics, Chapters 104–106—McGraw-Hill Book company, 1978, are useful, too, provided that the wavelength range is designed to be appropriate. A corresponding geometrical beam splitter can be construed by arranging spots or strips or intersecting strips of reflective coating, e.g. a mirror-like metallic coating, on a radiation transparent plate 71, e.g. on a sapphire-plate or a $CaF_2$-plate, whereupon the beam splitter 3 has a plurality of reflective spots 72 or strips or intersecting strips 73, i.e. areas D reflecting the radiation, and transparent intersecting strips 74 or strips or spots 75 respectively, i.e. areas C preferably transparent or possibly translucent to radiation, side by side within each of the common beam splitter areas A1 and A2, or A1–A4. Accordingly, there is transparent areas C and reflective areas D. In the geometrical beam splitter 3 the fields between the beam splitter areas A1 and A2, or A1–A4 common to the reflected beam portion $R_R$ and the respective transmitted beam portion $R_T$ may be without transparent areas, or may include transparent areas.

Figure 5:
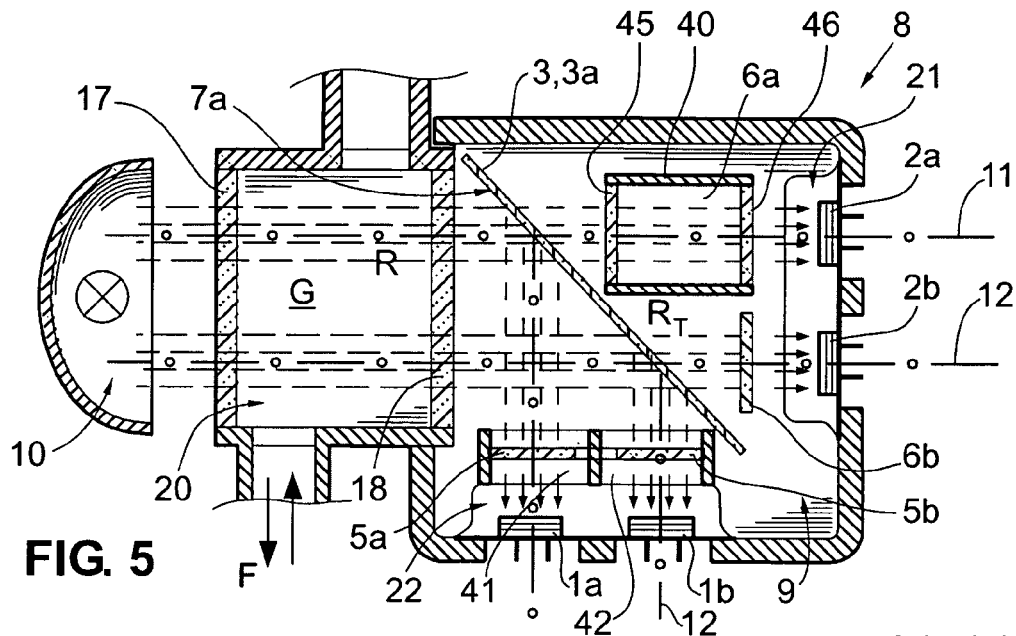
FIG. 5 represents schematically the fourth embodiment of the measuring arrangement including the detection assembly according to the invention, in the same view as in FIGS. 1 to 3.
Figure 6A:
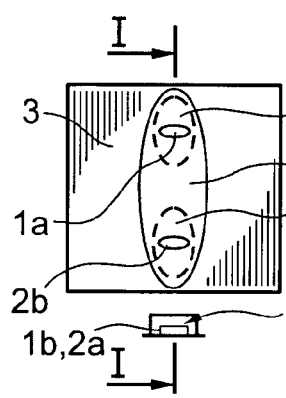
FIGS. 6A to 6C represents schematically the different lay-outs of the independent single path analyzer channels, specially on the beam splitter, and various configurations of the physical beam splitter, FIG. 6A in a direction II of FIG. 1, FIG. 6B in a direction III of FIG. 3 and FIG. 6C in a direction IV of FIG. 2 generally parallel to the radiation beams.
Figure 6B:
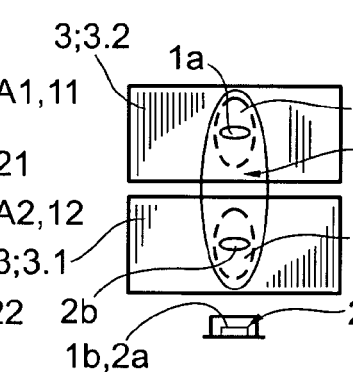
Figure 6C:
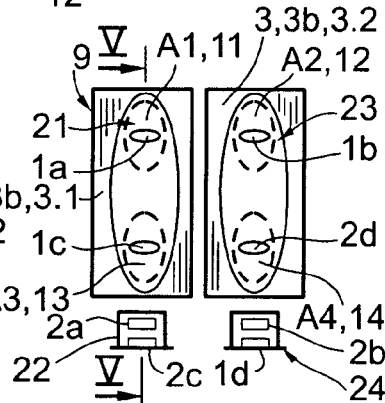
Figure 7:
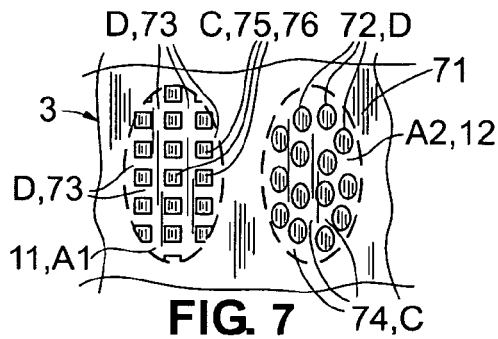
FIG. 7 represents two different surface configurations of a geometrical beam splitter useful for the measuring arrangement according to the invention, in the same view as FIGS. 6A to 6C but in larger scale.
Figure 8A:
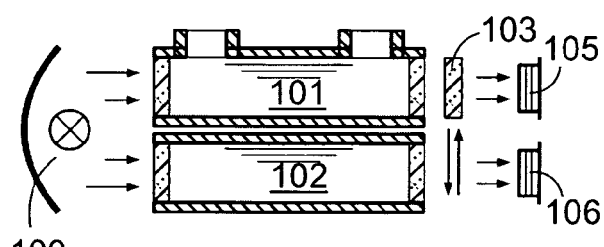
FIG. 8A to 8C show generally the arrangements for non-dispersive infrared analyzer according to the prior art.
Figure 8B:
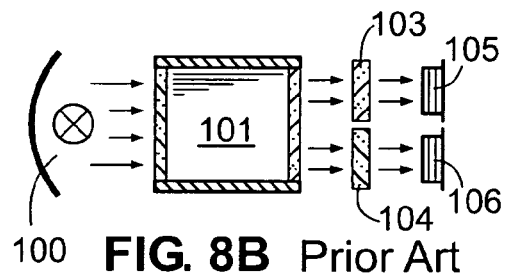
Figure 8C:
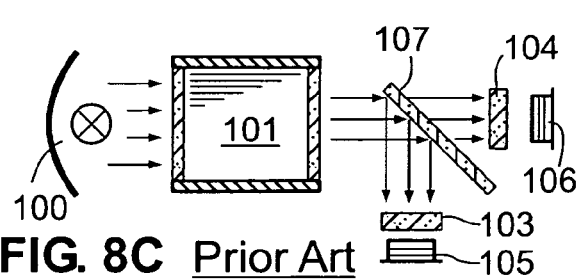

The preferred embodiments of the invention are shown in FIGS. 1 and 5. In these measuring arrangements 8 the radiation source 10 emits and directs a beam of broadband infrared radiation R through the measuring chamber 20 to the detection assembly. The emitted wavelengths can cover e.g. the range from 3 μm to 10 μm, or any other wavelength range depending on the application. The radiation source 10 can be an electrically heated filament. The measuring chamber 20 contains the gas mixture G comprising at least those gas components to be analyzed. In this case the gas mixture, being breathing gas, flows F from and to the patient through a connecting tube 19, and further from and to an anesthetic apparatus, not shown in the figure, and accordingly its is a main stream analyzer in question. Radiation coming from the radiation source enters the measuring chamber through the first window 17, passes through the sample gas mixture G and exits the measuring chamber through the second window 18. Radiation coming out of the measuring chamber 20 enters the detection assembly 9, in which the radiation R falls on the physical beam splitter 3, 3a at areas A1 and A2 as indicated in FIG. 6A or 6C that show the beam splitter seen in the direction towards the radiation source. A first portion of radiation R falling on area A1 of the beam splitter 3, 3a passes or is transmitted through the beam splitter and continues as the first transmitted beam portion $R_T$ through the first optical filter 5a and to the first detector 1a in the first detector unit 21, or through the first optical filter 6a and to the first detector 2a in the first detector unit 21. A second portion of the radiation coming to this area A1 is reflected by the beam splitter and continues as the first reflected beam portion $R_R$ through the second optical filter 6a and to the second detector 2a in the second detector unit 22, or through the second optical filter 5a and to the second detector 1a in the second detector unit 22. A third portion of the radiation falling on area A2 of the beam splitter 3, 3a passes or is transmitted through the beam splitter and continues as the third transmitted beam portion $R_T$ through the third optical filter 6b and to the third detector 2b in the first detector unit 21. A fourth portion of the radiation coming on area A2 is reflected by the beam splitter and continues as the fourth reflected beam portion $R_R$ through the fourth optical filter 5b and the fourth detector 1b in the second detector unit 22. So, after transmission through the optical filters 5a, 6a and 6b, 5b respectively, the radiation portions at the passbands or ranges of these filters fall on the radiation detector elements. In this case the beam splitter 3, 3a has even transmittance over the wavelength range utilized, whereupon the beam splitter typically has the construction of the partly transparent coatings not causing interference, or the construction of the boundary surface(s) of prism(s) or plate(s).

The first optical filter in the first detector unit 21 and the second optical filter in the second detector unit 22 are selected so that one of them is the measuring or measurement filter and the other is a suitable reference or reference filter. Thus in the alternative arrangement of FIG. 1, for the first single path analyzer channel 11 the first filter 5a together with the respective first detector 1a act as measurement partial channel, and the second filter 6a together with the respective second detector 2a act as reference partial channel. It shall be understood that the positions of the optical filters for attaining the measuring signals and the reference signals can be exchanged. Accordingly, in the alternative arrangement of FIG. 5, the first optical filter 6a together with the respective first detector 2a act as reference partial channel, and the second filter 5a together with the respective second detector 1a act as measurement partial channel respectively. In a corresponding way, the third optical filter in the first detector unit 21 and the fourth optical filter in the second detector unit 22 are selected so that one of them is the measuring filter and the other is a suitable reference filter. Thus in one alternative arrangement, for the second single path analyzer channel 12 the third filter 5b together with the respective third detector 1b act as measurement partial channel, and the fourth filter 6b together with the respective fourth detector 2b act as reference partial channel respectively. As above the optical filters can be exchanged here, too, whereupon the third filter 6b together with the respective third detector 2b act as reference partial channel, and the fourth filter 5b together with the respective fourth detector 1b act as measurement partial channel. It shall be noted that the latter part of the filter & detector reference numbers denote the analyzer channel, i.e. "-a" means the first analyzer channel and "-b" means the second analyzer channel, and that in the first part of the filter reference numbers "5" denote the measurement filter for attaining the measuring signal in the measurement partial channel and "6-" denote the reference filter for attaining the reference signal in the reference partial channel, and further that in the first part of the detector reference numbers "1-" denote the measurement partial channel and "2-" denote the reference partial channel. The detectors at least in each single path analyzer channel 11, 12 are preferably similar to each other, i.e. the detectors both for measurement partial channel and for reference partial channel of each single path analyzer channel having a common beam splitter area A1 or A2 have substantially the same electrical and optical properties. Of course individual variations can exist as any equipment. Different single path analyzer channel may have different type of detectors because of the different wavelengths used, and accordingly, the first single path analyzer channel 11 can have different detectors as compared to the detectors in the second single path analyzer channel 12.

The detection assembly in FIG. 1 includes two pairs of partial channels. Both of these pairs consist of a measurement partial channel and a corresponding reference partial channel. Both of the detectors for measurement channels can be located either in the first detector unit 21 or in the second detector unit 22 or one of them can be located in the first detector unit 21 and the other in the second detector unit 22, but the measurement channel and the respective reference channel of one pair, forming one single path analyzer channel, are arranged in different detector units. As can be understood, the radiation falling on the these two detectors in separate detector units originates from the same beam or beam section gone through the same volume of measuring chamber 20, and so form a single path analyzer channel. To express more specifically, each single path analyzer channel or analyzer path 11 and 12 comprises at least one measurement partial channel and one reference partial channel described above, i.e. at least two partial channels. The detection assembly can, of course, be provided with more than two single path analyzer channels or single analyzer paths.

If the detectors or detector elements operate only at non-zero frequencies, the electric input power to the radiation source can be modulated so that there is a non-zero frequency component in the radiation source output. FIG. 1 shows also the alternative of invention with a chopper unit between the radiation source 10 and the measuring chamber 20. The detector unit 9 can be similar to the detector unit described above or similar to any detector unit described below. A chopper unit typically consists of a rotating disc 23 with a number of openings, and an electric motor 24. As the disc rotates, the optical path from the radiation source to the detection assembly is alternatively opened and blocked. Thus, the radiation power has a non-zero frequency component that is necessary when the detector elements are for example of the Lead Selenide or Pyroelectric type.

Figure 2:
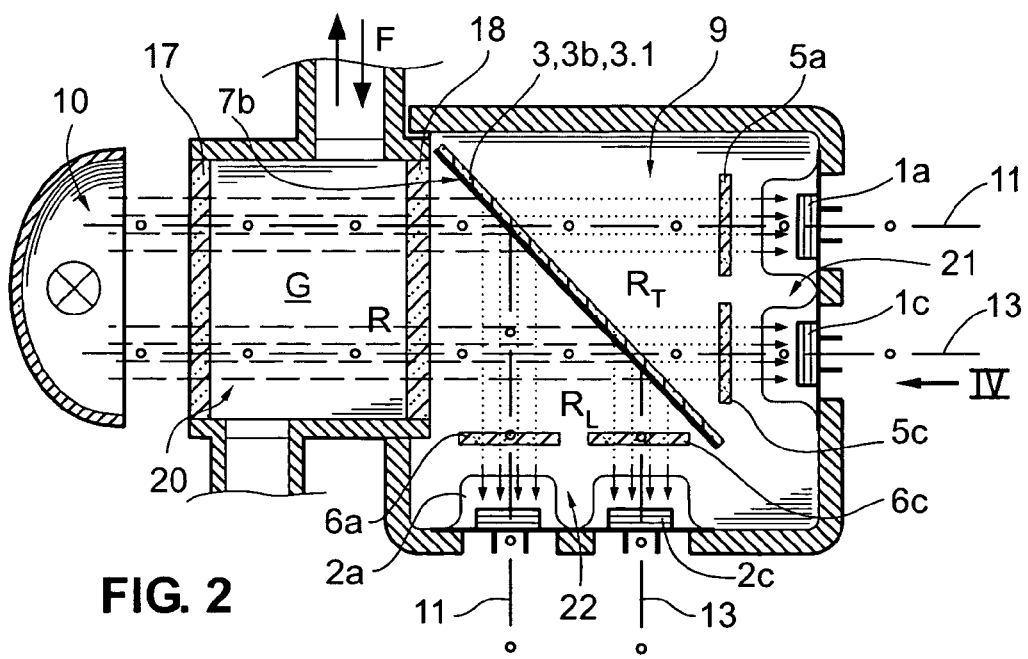
FIG. 2 represents schematically the second embodiment of the measuring arrangement including the detection assembly according to the invention, in mainly longitudinal section V of FIG. 6C parallel to the radiation beams.

Another embodiment of the invention is shown in FIG. 2. In this embodiment, the splitting ratio of the beam splitter 3, or the beam splitter segment 3.1, is wavelength dependent so that radiation at a first wavelength range passes the beam splitter to the first detector unit 21 and radiation at a second wavelength range is reflected to the second detector unit 22. In this case the beam splitter 3=3b or the first beam splitter segment 3.1 has variable transmittance over the wavelength range utilized, whereupon the beam splitter has the construction of the dichroic coating, the beam splitter is actually a single optical interference filter. It is most preferred that beam splitter 3 has highpass properties $I_H$ or lowpass properties $I_L$. In the case of highpass, whereupon the lower wavelength range not transmitted, i.e. with the reflectance characteristics $I_{RH}$, can preferably be from 3 μm to 5 μm and the higher wavelength range with transmittance can preferably be from 6 μm to 11 atm, as shown in FIG. 4A. The optical filters in the first detector unit 21, i.e. the first filter 1*a* and the third filter 1*c*, are then selected so that their passbands $I_B$ are between 6 and 11 μm and the optical filters for the second detector unit 22, i.e. the second filter 2*a* and the fourth filter 2*c*, are selected so that their passband is between 3 and 5 μm. As above, the first optical filter 5*a*, or 6*a* in the alternative case not shown, in the first detector unit 21 and the second optical filter 6*a*, or 5*a* in the alternative case not shown, in the second detector unit 22 are selected so that one of them is the measuring filter and the other is a suitable reference filter, and the third optical filter 5*c*, or 6*c* in the alternative case not shown, in the first detector unit 21 and the fourth optical filter 6*c*, 5*c* in the alternative case not shown, in the second detector unit 22 are selected so that one of them is the measuring filter and the other is a suitable reference filter. This way two measurement partial channels and two corresponding reference partial channels are formed, too, providing at least two single path analyzer channels 11 and 13 respective to two beam splitter areas A1 and A3. This embodiment has the advantage that the radiation power inputs to the detector elements at the passbands of the optical filters are bigger than with a beam splitter whose splitting ratio does not depend on wavelength.

The embodiment of FIG. 2 further comprises two additional single path analyzer channels 12 and 14 respective to two further beam splitter areas A2 and A4, as visible from FIG. 6C, whereupon the second beam splitter segment 3.2 of the beam splitter 3, 3*b* is on the side of the first beam splitter segment 3.1. The second beam splitter segment 3.2 can be wavelength dependent, too, so that radiation at a third wavelength range passes the beam splitter to the third detector unit 23 and radiation at a fourth wavelength range is reflected to the fourth detector unit 24. The transmitted and reflected wavelength ranges can be different from those of the first beam splitter segment, e.g. in case of lowpass the lower wavelength range with transmittance $I_L$ can be from 3 to 6 μm and the higher wavelength range not transmitted, i.e. with the reflectance characteristics $I_{RL}$, can be from 7 to 11 μm, as shown in FIG. 4B. The cross-over wavelength between the range of transmittance and the range of reflectance is about 6.5 μm. FIG. 4B shows also highpass $I_H$ characteristics from 9 to 11 μm and the reflectance characteristics $I_{RH}$ from 3 to 8 μm for the beam splitter, the cross-over wavelength being about 8.5 μm. After transmittance through and reflecting from the beam splitter the radiation portions $R_T$ and $R_R$ goes through the optical measurement filters and the optical reference filters in both single path analyzer channels 12 and 14, and fall to the detectors 1*b* and 2*b*, and to the detectors 1*d* and 2*d* respectively. As above, the optical filters for the third detector unit 23 and the optical filters for the fourth detector unit 24 are selected so that one of them is the measuring filter and the other is a suitable reference filter.

Figure 3:
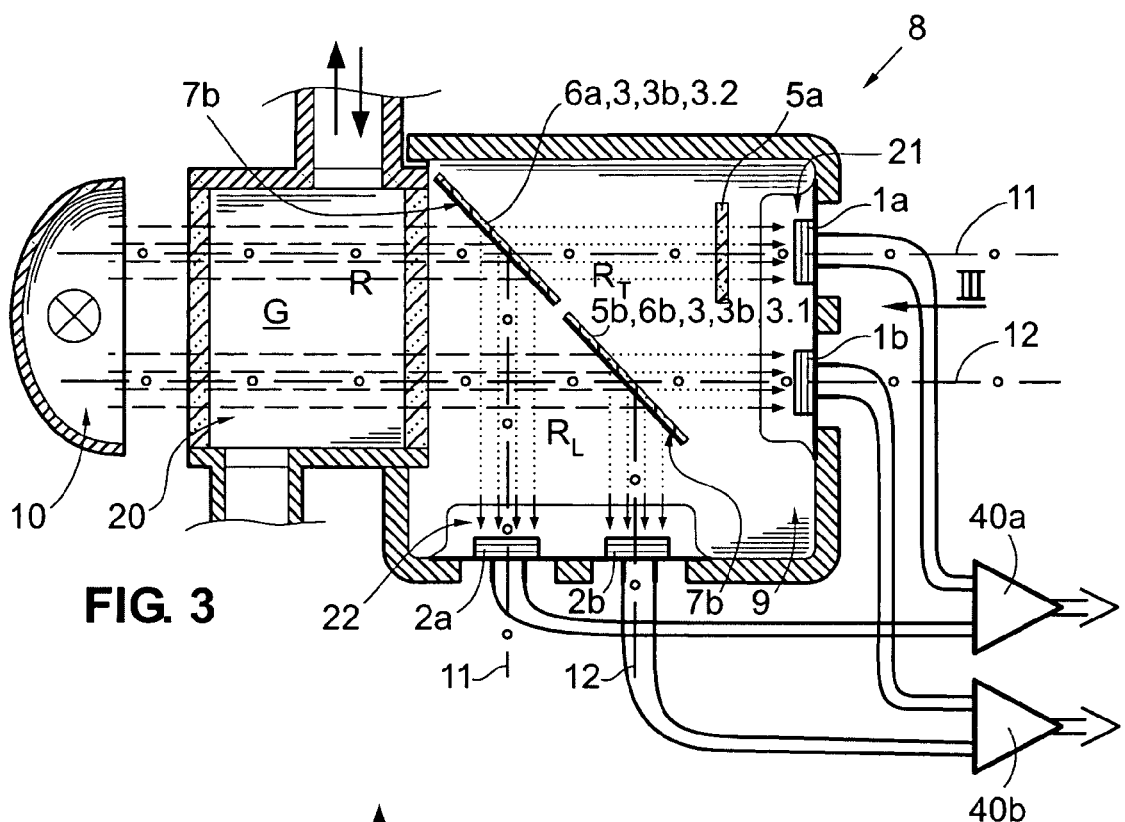
FIG. 3 represents schematically the third embodiment of the measuring arrangement including the detection assembly with signal connections according to the invention, in the same view as in FIGS. 1 and 2.

Further embodiment of the invention is shown in FIG. 3. Here the beam splitter 3 also consists of two segments 3.1 and 3.2 positioned on top of each other in a direction transversal to the beam direction of the radiation R, which beam splitter segments 3.1, 3.2 are designed and manufactured to have different beam splitting ratios. Here, for the second independent single path analyzer channel 12, the characteristics of the first beam splitter segment, i.e. the splitting ratio and the cross-over wavelength, are selected so that neither an additional measurement filter nor an additional reference filter is needed, but the beam splitter 3=3*b*, 3.1 acts simultaneously as the actual beam splitter 3 and as the measurement filter and as the reference filter. This is possible when the beam splitter 3 has the bandpass characteristics $I_B$ corresponding to the absorption peak of the measured gas component, and the gas component does not have any other substantial absorption peak in the wavelength range, where the detector has sensitivity and/or the chamber windows 17, 18 have transmittance and/or the radiation source 10 has emission. The beam splitting ratios can be optimized to have maximal radiation input to each of the optical filters. The first independent single path analyzer channel 11 is provided with an optical measurement filter 5*a*, having a narrow passband, but no additional reference filter. This kind of arrangement can be used when the beam splitter segment 3.2 has a relatively narrow wavelength range, which is reflected to have a proper wavelength range for the reference partial channel, whereupon the transmitted wavelength range is in many cases too wide necessitating the measurement filter. FIG. 3 also discloses the electronic processing units 40*a*, 40*b* for the two single path analyzer channels 11 and 12, whereupon the measurement partial channel and the corresponding reference partial channel of both analyzer channels, more specifically the detectors 1*a*+2*a* and 1*b*+2*b* respectively, is connected to one of the electronic processing units 40*a* or 40*b* to provide the measurement signals and the reference signals thereto. The electronic processing units are known as such, and can be of any known or new construction, and have any known or new operating or calculating principle. Accordingly, the electronic processing units are described in detail.

In the embodiment shown in FIG. 5, the beam splitter 3 and the detector units 21 and 22 can be any of those described in the embodiments of FIGS. 1 to 3. In this embodiment, radiation conducting tubes 40, 41, 42 are used for maximizing the amount of radiation that is gathered from the measuring chamber's exit side to the detectors and/or for providing only such rays of the radiation beam to fall to the optical filters, which have an angle of incidence smaller than a predetermined value. This kind of tubes is known as light guides, too. This way any shift of bandpass wavelengths is avoided. The radiation conducting tubes are holes with radiation reflecting inner surfaces, whereupon rays closer to parallelism with the length of the tubes or holes are reflected from the inner surface of the hole towards the optical filter and the detector, but the rays closer to perpendicularity to the length of the tubes or holes are absorbed by the inner surface of the hole preventing those rays from reaching the optical filter and the detector. It is clear that light conducting tubes can be used for all independent single path analyzer channel and for both the measuring partial channel and the reference partial channel, or some of the independent single path analyzer channels or some of the measuring partial channels and/or the reference partial channels, or all but one of the measuring partial channels or the reference partial channels can be without light conducting tubes. For example, reference partial channel with the optical reference filter 6*b* is left without radiation conducting tubes, and the rest of the measuring partial channels and the reference partial channels are provided with radiation conducting tubes, in the example of FIG. 5. In this case, the second detector unit 22 is provided with a common tube piece with two holes, but it shall be understood that a single common hole can be also used. In the embodiment of FIG. 5 one tube 40 of the radiation conducting tubes simultaneously constitutes the optical reference filter 6a, too. In this case the tube has ends, which are closed by the radiation transparent windows 45, 46 and filled with that gas component, which is analyzed by the measurement filter 5a and the detector 1a of the same independent single path analyzer channel 11.

In practice, the detection assemblies 9 according to the invention can be construed and built as shown in FIG. 1. Here the detection assembly consists of two body pieces 91 and 92, which can be manufactured separately and the attached to each other to form the frame of a detection assembly 9. The beam splitter or beam splitters or beam splitter segments 3, 3a, 3b, 3.1, 3.2 is/are placed between the body pieces 91, 92, though typically attached to one of the body pieces, and each of the detector units 21, 22 or 21–24 are assembled to their respective body pieces to receive the transmitted radiation $R_T$ and the reflected radiation $R_R$ from the beam splitter. Other types of construction can be also used.

It shall be understood that the measuring arrangement 8 according to the invention can also comprise optical filters and detectors, which are not selected and arranged according to the invention. The measuring arrangement 8 and the detection assembly 9, which is a part of the measuring arrangement, according to the invention anyway comprise at least two independent single path analyzer channels, each of which being provided with at least one measuring partial channel and one reference partial channel. The measuring partial channel and the reference partial channel of each independent single path analyzer channel receives radiation from the same area of the beam splitter 3 and from the same volume of the measuring chamber 20.

The invention claimed is:

1. A detection assembly for a non-dispersive infrared multigas analyzer, comprising: a beam splitter for dividing an IR-radiation beam into at least one reflected beam portion and at least one transmitted beam portion, at least a first and a second detector unit both with at least two separate detectors respectively, and optical filters in front of said detectors; said detector units being positioned to receive said at least one reflected beam portion and said at least one transmitted beam portion respectively, wherein:
   said first detector unit and said second detector unit both have at least one first detector, said first detectors being measuring detectors each provided with an optical measurement filter, which has a transmission wavelength band in the range of the absorption band of a gas component, so as to affect that portion of the IR-radiation ending into said first detector; and
   said first detector unit and said second detector unit both have at least one second detector, said second detectors being reference detectors each provided with an optical reference filter, which has a transmission wavelength range, within which said gas component does not have a substantial absorption, so as to affect that portion of the IR-radiation ending into said second detector; and that
   said first detector in said first detector unit and said second detector in said second detector unit are positioned to constitute a first independent single path analyzer channel, and said second detector in said first detector unit and said first detector in said second detector unit are positioned to constitute a second independent single path analyzer channel.

2. A detection assembly according to claim 1, wherein a first detector and a second detector constituting an independent single path analyzer channel are detector pairs.

3. A detection assembly according to claim 1, comprising a number of independent single path analyzer channels, and said number is at least equal to the number of those gas components to be analyzed.

4. A detection assembly according to claim 1, wherein said optical measurement filters are passband interference filters positioned:
   between said beam splitter and said first detectors; or
   to form said beam splitter.

5. A detection assembly according to claim 1, wherein said optical reference filters are selected from a group of filters including bandpass interference filters, and highpass interference filters, and lowpass interference filters, and gaseous filters providing attenuation of at least those wavelengths utilized for analysis.

6. A detection assembly according to claim 1, wherein said beam splitter is a physical beam splitter.

7. A detection assembly according to claim 6, wherein said physical beam splitter is a semi-transparent mirror proving a substantially even wavelength distribution both to said reflected beam portion and to said transmitted beam portion.

8. A detection assembly according to claim 6, wherein said physical beam splitter is an interference filter having bandpass or highpass or lowpass or bandlimiting characteristics to said transmitted beam portion and inverse characteristics to said reflected beam portion respectively.

9. A detection assembly according to claim 6, wherein said beam splitter comprises at least two splitter segments side by side, or on top of each other, one splitter segment for one or more independent single path analyzer channel.

10. A detection assembly according to claim 9, wherein said at least two splitter segments have different transmission characteristics.

11. A detection assembly according to claim 10, wherein each of said at least two splitter segments is a semi-transparent mirror providing a substantially even wavelength distribution both to said reflected beam portion and to said transmitted beam portion.

12. A detection assembly according to claim 10, wherein each of said at least two splitter segments is an interference filter having bandpass characteristics to said transmitted beam portion and inverse characteristics to said reflected beam portion respectively.

13. A detection assembly according to claim 10, wherein each of said at least two splitter segments is an interference filter having highpass characteristics to said transmitted beam portion and inverse characteristics to said reflected beam portion respectively.

14. A detection assembly according to claim 10, wherein each of said at least two splitter segments is an interference filter having lowpass characteristics to said transmitted beam portion and inverse characteristics to said reflected beam portion respectively.

15. A detection assembly according to claim 10, wherein each of said at least two splitter segments is an interference filter having bandlimiting characteristics to said transmitted beam portion and inverse characteristics to said reflected beam portion respectively.

16. A detection assembly according to claim 10, wherein at least one of said splitter segments has characteristics of said optical measurement filter to said transmitted beam portion, or inverse characteristics of said optical measurement filter to said reflected beam portion.

17. A detection assembly according to claim 1, wherein said beam splitter is a geometrical beam splitter having a plurality of radiation transparent areas and/or a plurality of radiation reflective areas within each beam splitter area common to said transmitted beam portion and said reflected beam portion.

18. A detection assembly for a non-dispersive infrared multigas analyzer, comprising: a beam splitter for dividing an IR-radiation beam into at least one reflected beam portion and at least one transmitted beam portion, at least a first and a second detector unit both with at least two separate detectors respectively, and optical filters in front of said detectors; said detector units being positioned to receive said at least one reflected beam portion and said at least one transmitted beam portion respectively, wherein:
  said first detector unit has at least two first detectors, said first detectors being measuring detectors each provided with an optical measurement filter, which has a transmission wavelength band in the range of the absorption band of a gas component, so as to affect that portion of the IR-radiation ending into said first detector; and
  said second detector unit has at least two second detectors, said second detectors being reference detectors each provided with an optical reference filter, which has a transmission wavelength range, within which said gas component does not have a substantial absorption, so as to affect that portion of the IR-radiation ending into said second detector; and that
  said first detector in said first detector unit and said second detector in said second detector unit are positioned to constitute a first independent single path analyzer channel, and said second detector in said first detector unit and said first detector in said second detector unit are positioned to constitute a second independent single path analyzer channel.

19. A detection assembly according to claim 18, wherein a first detector and a second detector constituting an independent single path analyzer channel are detector pairs.

20. A detection assembly according to claim 18, comprising a number of independent single path analyzer channels, and said number is at least equal to the number of those gas components to be analyzed.

21. A detection assembly according to claim 18, wherein said optical measurement filters are passband interference filters positioned:
  between said beam splitter and said first detectors; or
  to form said beam splitter.

22. A detection assembly according to claim 18, wherein said optical reference filters are selected from a group of filters including bandpass interference filters, and highpass interference filters, and lowpass interference filters, and gaseous filters providing attenuation of at least those wavelengths utilized for analysis.

23. A detection assembly according to claim 18, wherein said beam splitter is a physical beam splitter.

24. A detection assembly according to claim 23, wherein said physical beam splitter is a semi-transparent mirror proving a substantially even wavelength distribution both to said reflected beam portion and to said transmitted beam portion.

25. A detection assembly according to claim 23, wherein said physical beam splitter is an interference filter having bandpass or highpass or lowpass or bandlimiting characteristics to said transmitted beam portion and inverse characteristics to said reflected beam portion respectively.

26. A detection assembly according to claim 23, wherein said beam splitter comprises at least two splitter segments side by side, or on top of each other, one splitter segment for one or more independent single path analyzer channel.

27. A detection assembly according to claim 26, wherein said at least two splitter segments have different transmission characteristics.

28. A detection assembly according to claim 27, wherein each of said at least two splitter segments is a semi-transparent mirror providing a substantially even wavelength distribution both to said reflected beam portion and to said transmitted beam portion.

29. A detection assembly according to claim 27, wherein each of said at least two splitter segments is an interference filter having bandpass characteristics to said transmitted beam portion and inverse characteristics to said reflected beam portion respectively.

30. A detection assembly according to claim 27, wherein each of said at least two splitter segments is an interference filter having highpass characteristics to said transmitted beam portion and inverse characteristics to said reflected beam portion respectively.

31. A detection assembly according to claim 27, wherein each of said at least two splitter segments is an interference filter having lowpass characteristics to said transmitted beam portion and inverse characteristics to said reflected beam portion respectively.

32. A detection assembly according to claim 27, wherein each of said at least two splitter segments is an interference filter having bandlimiting characteristics to said transmitted beam portion and inverse characteristics to said reflected beam portion respectively.

33. A detection assembly according to claim 27, wherein at least one of said splitter segments has characteristics of said optical measurement filter to said transmitted beam portion, or inverse characteristics of said optical measurement filter to said reflected beam portion.

34. A detection assembly according to claim 18, wherein said beam splitter is a geometrical beam splitter having a plurality of radiation transparent areas and/or a plurality of radiation reflective areas within each beam splitter area common to said transmitted beam portion and said reflected beam portion.

35. A non-dispersive infrared measuring arrangement in a multigas analyzer, comprising:
  a radiation source providing an IR-radiation beam;
  a measuring chamber for receiving a gas mixture to be analyzed, and adapted to transmission of said radiation beam;
  a beam splitter dividing said beam into at least one reflected beam portion and at least one transmitted beam portion;
  at least a first and a second detector unit both with at least two detectors; and
  optical filters positioned in said beam or beam portions ending in said detectors, said detector units being directed to receive said at least one reflected beam portion and said at least one transmitted beam portion respectively, wherein:
  said first detector unit and said second detector unit both have at least one first detector, said first detectors being measuring detectors each provided with an optical measurement filter, said filters having transmission wavelength bands adapted to detection of the concentration of a gas component in said gas mixture; and
  said first detector unit and said second detector unit both have at least one second detector, said second detectors being reference detectors each provided with an optical reference filter, said filters having transmission wavelength ranges, within which said gas component does not have substantial absorption; and said first detector in said first detector unit and said second detector in said second detector unit are positioned to constitute a first independent single path analyzer channel, and said second detector in said first detector unit and said first detector in said second detector unit are positioned to constitute a second independent single path analyzer channel.

36. A measuring arrangement according to claim 35, wherein said multigas analyzer is a mainstream analyzer.

37. A measuring arrangement according to claim 35, wherein said first detector and said second detector constituting an independent single path analyzer channel are positioned and directed towards a common beam splitter area, which divides said radiation beam or a section thereof transmitted through said measuring chamber into said first and second detector.

38. A measuring arrangement according to claim 35, wherein said measuring arrangement comprises a number of independent single path analyzer channels, and said number is at least equal to the number of those gas components to be analyzed in said gas mixture.

39. A measuring arrangement according to claim 35, wherein said optical measurement filters are interference filters selected from a group of optical filters including bandpass interference filters, and highpass interference filters, and lowpass interference filters, and gaseous filters providing attenuation of at least those wavelengths utilized for analysis.

40. A measuring arrangement according to claim 35, wherein said beam splitter is a physical beam splitter.

41. A measuring arrangement according to claim 40, wherein said physical beam splitter is a semi-transparent mirror proving a substantially even wavelength distribution both to said reflected and transmitted beam portions.

42. A measuring arrangement according to claim 40, wherein said physical beam splitter is an interference filter having bandpass or highpass or lowpass or bandlimiting characteristics to said transmitted beam portion and inverse characteristics to said reflected beam portion respectively.

43. A measuring arrangement according to claim 40, wherein said beam splitter comprises at least two splitter segments side by side, or on top of each other, one splitter segment for one or more independent single path analyzer channel.

44. A measuring arrangement according to claim 43, wherein said at least two splitter segments have different transmission characteristics.

45. A measuring arrangement according to claim 44, wherein each of said at least two splitter segments is a semi-transparent mirror providing a substantially even wavelength distribution both to said reflected beam portion and to said transmitted beam portion.

46. A measuring arrangement according to claim 44, wherein each of said at least two splitter segments is an interference filter having bandpass characteristics to said transmitted beam portion and inverse characteristics to said reflected beam portion respectively.

47. A measuring arrangement according to claim 44, wherein each of said at least two splitter segments is an interference filter having highpass characteristics to said transmitted beam portion and inverse characteristics to said reflected beam portion respectively.

48. A measuring arrangement according to claim 44, wherein each of said at least two splitter segments is an interference filter having lowpass characteristics to said transmitted beam portion and inverse characteristics to said reflected beam portion respectively.

49. A measuring arrangement according to claim 44, wherein each of said at least two splitter segments is an interference filter having bandlimiting characteristics to said transmitted beam portion and inverse characteristics to said reflected beam portion respectively.

50. A measuring arrangement according to claim 44, wherein at least one of said splitter segments has characteristics of said optical measurement filter to said transmitted beam portion, or inverse characteristics of said optical measurement filter to said reflected beam portion.

51. A measuring arrangement according to claim 35, further comprising electronic processing units each of which being connected to said first detector and said second detector of each independent single path analyzer channel.

52. A measuring arrangement according to claim 35, further comprising radiation-conducting tubes in at least a measuring partial channel or a reference partial channel of one independent single path analyzer channel.

53. A measuring arrangement according to claim 35, wherein said beam splitter is a geometrical beam splitter having a plurality of radiation transparent areas and/or a plurality of radiation reflective areas within each beam splitter area common to said transmitted beam portion and said reflected beam portion.

54. A non-dispersive infrared measuring arrangement in a multigas analyzer, comprising:

a radiation source providing an IR-radiation beam;

a measuring chamber for receiving a gas mixture to be analyzed, and adapted to transmission of said radiation beam;

a beam splitter dividing said beam into at least one reflected beam portion and at least one transmitted beam portion;

at least a first and a second detector unit both with at least two detectors, and optical filters positioned in said beam or beam portions ending in said detectors, said detector units being directed to receive said at least one reflected beam portion and said at least one transmitted beam portion respectively, wherein:

said first detector unit has at least two first detectors, said first detectors being measuring detectors each provided with an optical measurement filter, said filters having transmission wavelength bands adapted to detection of the concentration of a gas component in said gas mixture; and said second detector unit has at least two second detectors, said second detectors being reference detectors each provided with an optical reference filter, said filters having transmission wavelength ranges, within which said gas component does not have substantial absorption; and said first detector in said first detector unit and said second detector in said second detector unit are positioned to constitute a first independent single path analyzer channel, and said second detector in said first detector unit and said first detector in said second detector unit are positioned to constitute a second independent single path analyzer channel.

55. A measuring arrangement according to claim 54, wherein said multigas analyzer is a mainstream analyzer.

56. A measuring arrangement according to claim 54, wherein said first detector and said second detector constituting an independent single path analyzer channel are positioned and directed towards a common beam splitter area, which divides said radiation beam or a section thereof transmitted through said measuring chamber into said first and second detector.

57. A measuring arrangement according to claim 54, wherein said measuring arrangement comprises a number of independent single path analyzer channels, and said number is at least equal to the number of those gas components to be analyzed in said gas mixture.

58. A measuring arrangement according to claim 54, wherein said optical measurement filters are interference filters selected from a group of optical filters including bandpass interference filters, and highpass interference filters, and lowpass interference filters, and gaseous filters providing attenuation of at least those wavelengths utilized for analysis.

59. A measuring arrangement according to claim 54, wherein said beam splitter is a physical beam splitter.

60. A measuring arrangement according to claim 59, wherein said physical beam splitter is a semi-transparent mirror proving a substantially even wavelength distribution both to said reflected and transmitted beam portions.

61. A measuring arrangement according to claim 59, wherein said physical beam splitter is an interference filter having bandpass or highpass or lowpass or bandlimiting characteristics to said transmitted beam portion and inverse characteristics to said reflected beam portion respectively.

62. A measuring arrangement according to claim 59, wherein said beam splitter comprises at least two splitter segments side by side, or on top of each other, one splitter segment for one or more independent single path analyzer channel.

63. A measuring arrangement according to claim 62, wherein said at least two splitter segments have different transmission characteristics.

64. A measuring arrangement according to claim 63, wherein each of said at least two splitter segments is a semi-transparent mirror providing a substantially even wavelength distribution both to said reflected beam portion and to said transmitted beam portion.

65. A measuring arrangement according to claim 63, wherein each of said at least two splitter segments is an interference filter having bandpass characteristics to said transmitted beam portion and inverse characteristics to said reflected beam portion respectively.

66. A measuring arrangement according to claim 63, wherein each of said at least two splitter segments is an interference filter having highpass characteristics to said transmitted beam portion and inverse characteristics to said reflected beam portion respectively.

67. A measuring arrangement according to claim 63, wherein each of said at least two splitter segments is an interference filter having lowpass characteristics to said transmitted beam portion and inverse characteristics to said reflected beam portion respectively.

68. A measuring arrangement according to claim 63, wherein each of said at least two splitter segments is an interference filter having bandlimiting characteristics to said transmitted beam portion and inverse characteristics to said reflected beam portion respectively.

69. A measuring arrangement according to claim 63, wherein at least one of said splitter segments has characteristics of said optical measurement filter to said transmitted beam portion, or inverse characteristics of said optical measurement filter to said reflected beam portion.

70. A measuring arrangement according to any of claims 54, further comprising electronic processing units each of which being connected to said first detector and said second detector of each independent single path analyzer channel.

71. A measuring arrangement according to any of claims 54, further comprising radiation-conducting tubes in at least a measuring partial channel or a reference partial channel of one independent single path analyzer channel.

72. A measuring arrangement according to claim 54, wherein said beam splitter is a geometrical beam splitter having a plurality of radiation transparent areas and/or a plurality of radiation reflective areas within each beam splitter area common to said transmitted beam portion and said reflected beam portion.

* * * * *